United States Patent [19]

Terada et al.

[11] Patent Number: 5,639,862
[45] Date of Patent: Jun. 17, 1997

[54] DELETION MUTEINS OF HST-1

[75] Inventors: Masaaki Terada, Tokyo; Hiromi Sakamoto, Chiba; Teruhiko Yoshida, Tokyo; Koichi Igarashi, Kyoto; Yoshio Kozai, Osaka, all of Japan

[73] Assignees: President of National Cancer Center, Tokyo; Takeda Chemical Industries, Ltd., Osaka, both of Japan

[21] Appl. No.: 446,198

[22] Filed: May 19, 1995

Related U.S. Application Data

[63] Continuation of Ser. No. 6,869, Jan. 19, 1993, abandoned, which is a continuation of Ser. No. 589,913, Sep. 28, 1990, abandoned.

[30] Foreign Application Priority Data

| Oct. 6, 1989 | [JP] | Japan | 1-262331 |
| Oct. 19, 1989 | [JP] | Japan | 1-273036 |
| Nov. 21, 1989 | [JP] | Japan | 1-303607 |

[51] Int. Cl.⁶ .................. C07K 14/475; C07K 14/495
[52] U.S. Cl. .................. 530/399; 435/69.1; 435/69.4
[58] Field of Search .................. 530/399; 435/69.1, 435/69.4

[56] References Cited

FOREIGN PATENT DOCUMENTS 326907  8/1989  European Pat. Off. .

OTHER PUBLICATIONS

H. Sakamoto et al., *Proc. Nat'l. Acad. Sci. USA*, 83:3997–4001 (1986).

M. Taira et al., *Proc. Nat'l. Acad. Sci. USA*, 84:2980–2984 (1987).

T. Yoshida et al., *Proc. Nat'l. Acad. Sci. USA*, 84:7305–7309 (1987).

M. Toshida et al., *Proc. Nat'l. Acad. Sci. USA*, 85:4861–4864 (1988).

P. Bovi et al., *Cell* 50:729–737 (1987).

K. Miyagawa et al., *Oncogene*, 3:383–389 (1988).

P. Bovi et al., *Molecular and Cellular Biology*, 8:2933–2941 (1988).

W.E. Holmes et al., *Biotechnology*, 3:923–929 (1985).

K.A. Thomas, *FASEB Journal*, 1:6, pp. 434–440 (1987).

*Primary Examiner*—John L. LeGuyader
*Attorney, Agent, or Firm*—David G. Conlin; Linda M. Buckley

[57] ABSTRACT

A deletion type mutein of heparin-binding secretory transforming factor (hst-1) possesses excellent cell growth promoting activity and is stable. The present mutein can therefore be used as a therapeutic medicine such as a healing promoter for burns, wounds, surgical injuries etc.

4 Claims, 10 Drawing Sheets

FIG. 1

Pro Thr Ala Pro Asn Gly Thr Leu Glu
  1           5
Ala Glu Leu Glu Arg Arg Trp Glu Ser Leu
 10          15
Val Ala Leu Ser Leu Ala Arg Leu Pro Val
 20          25
Ala Ala Gln Pro Lys Glu Ala Ala Val Gln
 30          35
Ser Gly Ala Gly Asp Tyr Leu Leu Gly Ile
 40          45
Lys Arg Arg Leu Tyr Cys Asn Val Gly Ile
 50          55
Gly Phe His Leu Gln Ala Leu Pro Asp Gly
 60          65
Asp Gly Arg Ile Gly Gly Ala His Ala Asp
 70          75
Thr Arg Asp Ser Leu Glu Leu Ser Pro Val
 80          85
Glu Arg Gly Val Val Ser Ile Phe Gly Val
 90          95
Ala Ser Arg Phe Phe Val Ala Met Ser Ser
100         105
Lys Gly Lys Leu Tyr Gly Ser Pro Phe Phe
110         115
Thr Asp Glu Cys Thr Phe Lys Glu Ile Leu
120         125
Leu Pro Asn Asn Tyr Asn Ala Tyr Glu Ser
130         135
Tyr Lys Tyr Pro Gly Met Phe Ile Ala Leu
140         145
Ser Lys Asn Gly Lys Thr Lys Lys Gly Asn
150         155
Arg Val Ser Pro Thr Met Lys Val Thr
160         165
His Phe Leu Pro Arg Leu
170         175

FIG. 2

```
Met Ser Gly Pro Gly Thr Ala Ala Val Ala Leu Leu Pro Ala Val Leu Leu Ala Leu Leu
 1               5                  10                  15                  20
Ala Pro Trp Ala Gly Arg Gly Ala Ala Ala Pro Thr Ala Pro Asn Gly Thr Leu Glu
                25                  30                  35                  40
Ala Glu Leu Glu Arg Arg Trp Glu Ser Leu Val Ala Leu Ser Leu Ala Arg Leu Pro Val
                45                  50                  55                  60
Ala Ala Gln Pro Lys Glu Ala Ala Val Gln Ser Gly Ala Gly Asp Tyr Leu Leu Gly Ile
                65                  70                  75                  80
Lys Arg Leu Arg Arg Leu Tyr Cys Asn Val Gly Ile Gly Phe His Leu Gln Ala Leu Pro
                85                  90                  95                 100
Asp Gly Arg Ile Gly Gly Ala His Ala Asp Thr Arg Asp Ser Leu Leu Glu Leu Ser Pro
               105                 110                 115                 120
Val Glu Arg Gly Val Val Ser Ile Phe Gly Val Ala Ser Arg Phe Phe Val Ala Met Ser
               125                 130                 135                 140
Ser Lys Gly Lys Leu Tyr Gly Ser Pro Phe Phe Thr Asp Glu Cys Thr Phe Lys Glu Ile
               145                 150                 155                 160
Leu Leu Pro Asn Asn Tyr Asn Ala Tyr Glu Ser Tyr Lys Tyr Pro Gly Met Phe Ile Ala
               165                 170                 175                 180
Leu Ser Lys Asn Gly Lys Thr Lys Lys Gly Asn Arg Val Ser Pro Thr Met Lys Val Thr
               185                 190                 195                 200
His Phe Leu Pro Arg Leu
               205
```

FIG. 3

```
                                                                    Pro Val
                                                                      1
Ala Ala Gln Pro Lys Glu Ala Ala Val Gln Ser Gly Ala Gly Asp Tyr Leu Leu Gly Ile
              5              10             15             20

Lys Arg Leu Arg Arg Leu Tyr Cys Asn Val Gly Ile Gly Phe His Leu Gln Ala Leu Pro
             25              30             35             40

Asp Gly Arg Ile Gly Gly Ala His Ala Asp Thr Arg Asp Ser Leu Leu Glu Leu Ser Pro
             45              50             55             60

Val Glu Arg Gly Val Val Ser Ile Phe Gly Val Ala Ser Arg Phe Phe Val Ala Met Ser
             65              70             75             80

Ser Lys Leu Tyr Gly Ser Pro Phe Phe Thr Asp Glu Cys Thr Phe Lys Glu Ile
             85              90             95            100

Leu Leu Pro Asn Asn Tyr Asn Ala Tyr Lys Tyr Pro Gly Met Phe Ile Ala
            105             110            115            120

Leu Ser Lys Asn Gly Lys Lys Thr Lys Lys Gly Asn Arg Val Ser Pro Thr Met Lys Val Thr
            125             130            135            140

His Phe Leu Pro Arg Leu
            145
```

|       | 1 | 2 | 3 | 4 | 5 |
|-------|---|---|---|---|---|
| 92 500 → | — |   |   |   |   |
| 66 200 → | — |   |   |   |   |
| 45 000 → | — |   |   |   |   |
| 31 000 → | — |   |   |   |   |
| 21 500 → | ═ |   |   |   |   |
|       |   |   | ———————— |   |   |
| 14 400 → | — |   |   |   |   |

FIG. 8

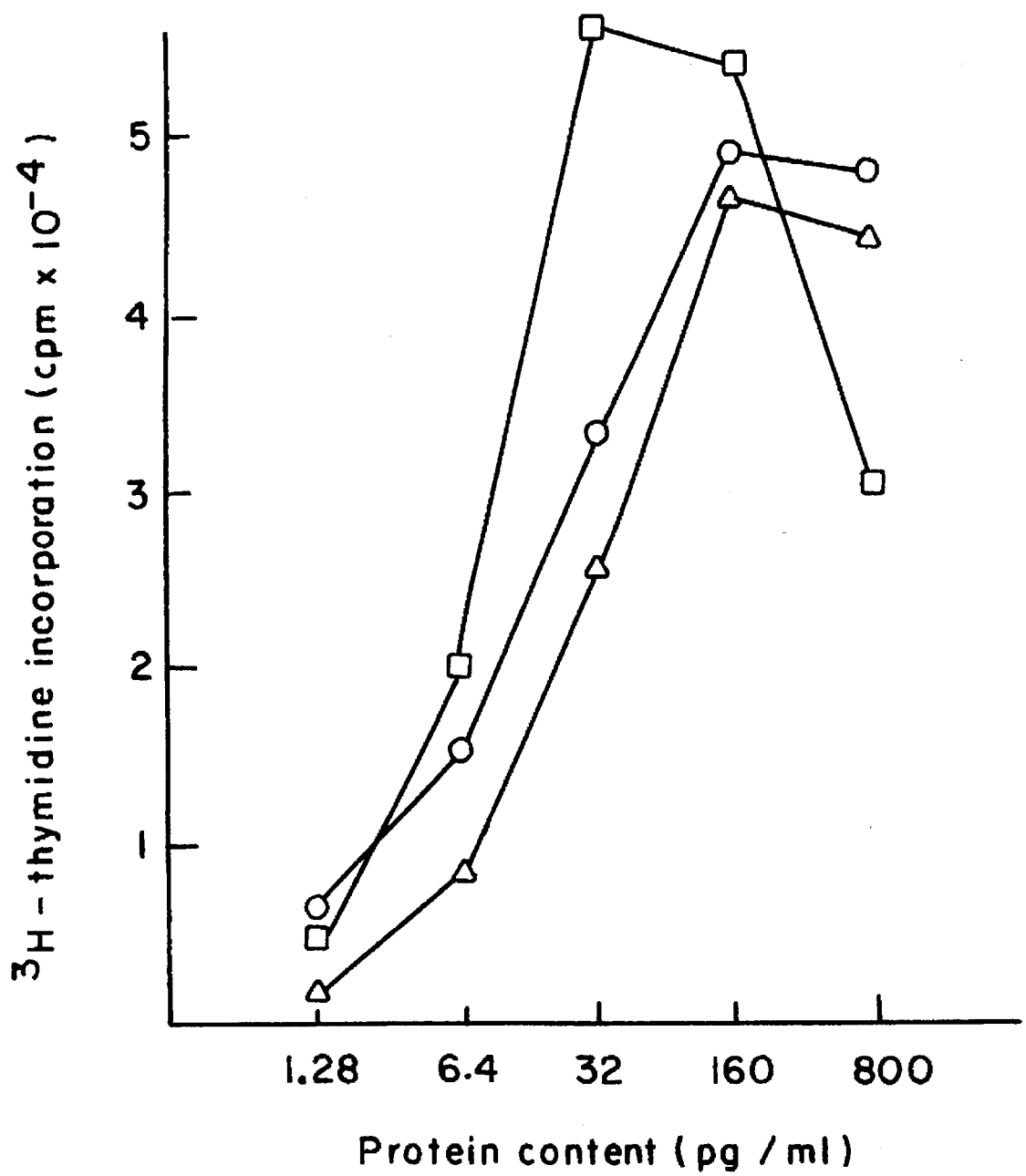
F I G. 10

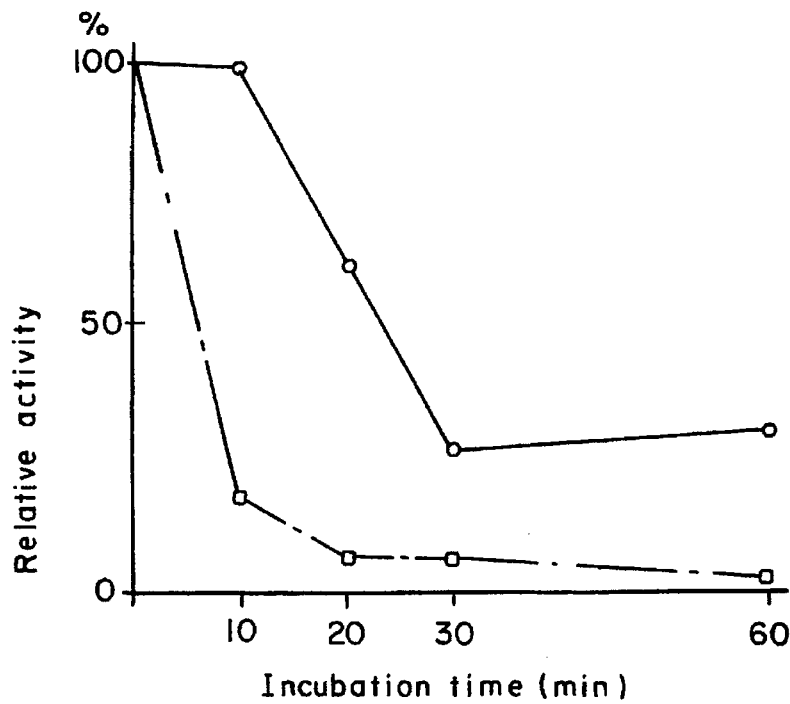
F I G. 12
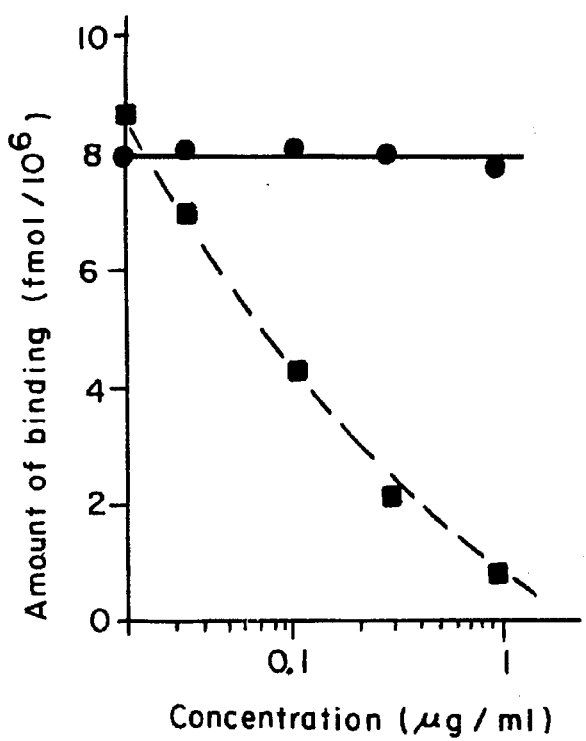
F I G. 13

DELETION MUTEINS OF HST-1

This is a continuation of application Ser. No. 08/006,869, filed on Jan. 19, 1993, now abandoned, which is a continuation of Ser. No. 07/589,913, filed Sep. 28, 1990, now abandoned.

The present invention relates to a deletion type mutein of heparin-binding secretory transforming factor (hereinafter also abbreviated hst-1) and a method of its production.

hst-1 is also referred to as HSTF1 [M. Yoshida et al.: Proc. Natl. Acad. Sci. USA, 85, 4861–4864 (1988)].

The hst-1 gene is a transforming gene isolated from human gastric cancer tissue [H. Sakamoto et al.: Proc. Natl. Acad. Sci. USA, 83, 3997 (1986)]. Its gene product has been found to be similar to fibroblast growth factor (FGF), a cell growth factor, in structure and bioactivities [T. Yoshida et al.: Proc. Natl. Acad. Sci. USA, 84, 7305 (1987); K. Miyagawa et al.: Oncogene, 3, 383 (1988)]. Also, the hst-1 gene has been isolated from large intestine cancer, hepatoma and Kaposi's sarcoma in AIDS patients as well as from gastric cancer [T. Koda et al.: Jpn. J. Cancer Res. (Gann) 78, 325 (1987); H. Nakagawa et al.: Jpn. J. Cancer Res. (Gann), 78, 651 (1987); Y. Yuasa et al.: Jpn. J. Cancer Res. (Gann), 78, 1036 (1987); P. Delli Bovi et al.: Cell, 50, 729 (1987)]. This gene is considered to form the FGF gene family together with basic FGF gene, acidic FGF gene, int-2 gene etc. The gene isolated from Kaposi's sarcoma described above is also called K-FGF. Since the hst-1 gene is a transforming gene that acts as a cell growth factor, as stated above, its gene product, like FGF, has potential for use as a preventive or therapeutic drug such as a remedy for trauma.

The base sequence of the hst-1 gene is already known [M. Taira et al.: Proc. Natl. Acad. Sci. USA, 84, 2980 (1987); T. Yoshida et al.: Proc. Natl. Acad. Sci. USA, 84, 7305 (1987)]. These reports specify the constituent amino acids of hst-1 deduced from this base sequence.

However, natural quantities of hst-1 are considered to be extremely small, and there is no report of obtaining hst-1 from live material.

On the other hand, there are some reports of the production of hst-1 by genetic engineering technology [P. Delli Bovi et al.: Cell, 50, 729 (1987); K. Miyagawa et al.: Oncogene, 3, 383 (1988)], but mass production is very difficult even in these cases.

As stated above, much remains unknown as to the nature and biological activities of hst-1. However, hst-1 has potential for use as a pharmaceutical or reagent.

As stated above, however, hst-1 has not yet been mass-produced.

With this background, the present inventors attempted to modify such hst-1 so that it becomes microbiologically mass-producible, without adverse influence on its activities, using genetic engineering technology, in consideration that this modification may result in hst-1 stabilization, increased cell growth activity per molecule and potentiation of unknown biological activities, as well as the increase in cellular productivity described above.

The present inventors investigated the increase in hst-1 mutein cellular productivity and activity and the change in biological activities by preparing an hst-1 mutein gene having a partial deletion, via recombinant DNA technology, and expressing it in microoranisms, and discovered a mutein that serves for the objectives described above. The present inventors made further investigations based on this finding, and developed the present invention.

Accordingly, the present invention comprises:
(1) A deletion type mutein of heparin-binding secretory transforming factor (hst-1),
(2) Recombinant DNA having a base sequence that encodes the mutein of (1) above,
(3) A vector containing the recombinant DNA of (2) above,
(4) A transformant carrying the vector of (3) above, and
(5) A method of producing the mutein of (1) above by cultivation of the transformant of (4) above in a culture medium.

The hst-1 which serves as the base for the deletion type mutein of the present invention is a protein comprising the 175 sequencial amino acids shown in FIG. 1.

In the literature [M. Taira et al.: Proc. Natl. Acad. Sci. USA, 84, 2980–2984 (1987)], hst-1 is described as comprising 206 amino acids, whose sequence is shown in FIG. 2. However, in Molecular and Cellular Biology, 8, 2933–2941 (1988), Delli-Bovi et al. show that when hst-1 is expressed in simian COS-1 cells (the desired product is called K-FGF), the resulting product lacks 30 or 31 N-terminal amino acids. It is therefore considered most reasonable to identify the matured hst-1 as having an amino acid sequence resulting from the elimination of 31 N-terminal amino acids from the above-mentioned sequence comprising 206 amino acids (shown in FIG. 1).

The deletion type mutein of the present invention lacks at least one of the constituent amino acid residues from hst-1 and possesses hst-1 activities.

Said deletion type mutein preferably lacks 1 to 47 continuous constituent amino acid residues of hst-1.

It is more preferable that the deletion type mutein of the present invention lacks 1 to 43 constituent amino acid residues of hst-1, most preferably the deleted type mutein of the present invention lacks 1 to 27 continuous constituent amino acid residues of hst-1.

The precise chemical structure of the deletion type hst-1 muteins of the present invention will depend upon a number of factors. For example, such muteins may be obtained as an acidic or basic salt or in neutral form. Moreover, the muteins may be derivatized with sugar moieties or by other entities such as lipids, acetyl groups and so forth. Furthermore, although such modifications, including the precise deletions, may affect the bioactivity of Applicants' deletion type hst-1 muteins, all such deletion type hst-1 muteins which retain their biological activity are included within the scope of the present invention.

The biological activities of the hst-1 deletion muteins of the present invention can be determined by the method of Sasada et al. [Sasada et al., *Mol. Cell Biol.*, 8, 588 (1988)] measuring the uptake of [$^3$H] thymidine as an index of induction of DNA synthesis in mouse BALB/c3T3 cells, by the MTT method of Tada et al. [Tada et al., *Journal of Immunological Methods*, 93, 157 (1986)] measuring the stimulation of the growth of vascular endothelial cells, or by the method of Auerbach [Auerbach, *Developmental Biology*, 41, 391 (1974)] measuring the angiogenesis on the chick embryo chorioallantoic membrane.

An expression vector containing DNA having a base sequence that encodes the mutein of the present invention can, for example, be produced by:
(1) Separating the RNA that encodes the hst-1 protein,
(2) Synthesizing single-stranded complementary DNA (cDNA) and then double-stranded DNA from the separated RNA,
(3) Inserting the complementary DNA into a plasmid,
(4) Transforming a host with the obtained recombinant plasmid,
(5) Cultivating the resulting transformant and isolating the plasmid containing the desired DNA therefrom by an appropriate method, e.g., the colony hybridization method using a DNA probe, (6) Cleaving out the desired cloned DNA form the plasmid, (7) Causing the desired deletion on the cloned DNA, (8) Coupling an oligonucleotide containing the ATG codon as desired, and (9) Ligating the DNA to a vehicle at a site downstream from a promoter present therein.

RNA that encodes hst-1 can be obtained from various human cancerous cells such as those of gastric cancer, large intestine cancer, hepatoma, Kaposi's sarcoma, human germ cell tumor and NIH3T3 transformant induced by the human hst-1 gene.

Examples of the method of preparing RNA from human cancer include the guanidine thiocyanate method [J. M. Chirgwin et al.: Biochemistry, 18, 5294 (1979)].

A cDNA library can be prepared by synthesizing a cDNA using the RNA thus obtained as a template, inserting it in, for example, λ phage vector λgt10 [Huynh, T. V. et al.: DNA Cloning, A Practical Approach, IRL Press, Oxford, p. 49 (1985)] in accordance with, for example, the method of Watson and Jackson [Watson, C. J. and Jackson J. F.: DNA Cloning, A Practical Approach, IRL Press, Oxford, p. 79 (1985)] and infecting it with *Escherichia coli*, e.g., C600 or Hf1A [Huynh, T. V. et al.: same as above].

From the cDNA library thus obtained are selected desired phage clones using methods known per se, such as the plaque hybridization method [Maniatis et al.: Moleclar Cloning, Cold Spring Harbor Laboratory, p. 320 (1982)] and the DNA base sequencing method [Proc. Natl. Acad. Sci. USA, 74, 560 (1977); Nucleic Acids Research, 9,309 (1981) ].

It is also advantageous to collect the phage clones, extract phage DNA by, for example, the method of Davis et al. [Davis et al.: Advanced Bacterial Genetics, Cold Spring Harbor Laboratory, (1980)], cut off its cDNA moiety using restriction enzyme and reinsert it into a plasmid such as pUC13 before use.

The cloned plasmid harboring DNA having a base sequence that encodes hst-1 described above is used with or without cleavage using restriction enzyme, as desired.

The cloned gene can be ligated to a vehicle (vector) suitable for expression in a site downstream from the promoter present therein, to yield an expression vector.

To produce the mutein of the present invention, site-directed mutagenesis is employed in addition to the conventional recombinant DNA technology. This technique, know to those skilled in the art, is described by R. F. Lather and J. P. Lecoq in Genetic Engineering, Academic Press, pp. 31–50 (1983). Oligonucleotide-directed mutagenesis is described by M. Smith and S. Gillam in Genetic Engineering, Principle and Methodology, Plenum Press, vol. 3, pp. 1–32 (1981).

A structural gene that encodes the mutein of the present invention can be produced by, for example, (a) Hybridizing single-stranded DNA, comprising a single strand of the structural gene of hst-1, with a mutagenic oligonucleotide primer, (b) Elongating the primer using DNA polymerase to form a mutated heteroduplex, and (c) Replicating the mutated heteroduplex.

The size of the oligonucleotide primer depends on the conditions necessary for stable hybridization of the primer to the gene region to be mutated, and the limitations of the currently available method of oligonucleotide synthesis. The factors to be considered in designing the oligonucleotide for oligonucleotide-directed mutagenesis (e.g., overall size, size of the oligonucleotide except mismatched nucleotide) are described by M. Smith and S. Gillam (mentioned above). In general, the total length of the oligonucleotide should be such that stable and unique hybridization at the mutagenesis site is optimized, with the extensions between the mutagenesis site and the 5'- and 3'-terminals having sufficient length to avoid mutagenesis editing by the exonuclease activity of DNA polymerase. The oligonucleotide used for mutagenesis in accordance with the present invention normally contains about 12 to 24 bases, preferably about 14 to 20 bases, more preferably about 14 to 18 bases, which include at least 3 3'-terminal bases of the codon to be changed.

The following three methods are available for preparing a mutant hst-1 gene fro the purpose of obtaining a mutein lacking a constituent amino acid of hst-1: In the first method, a deletion is caused in the amino terminal of hst-1. In the second method, a deletion is caused in the middle portion of hst-1. In the third method, a deletion is caused in the carboxyl terminal of hst-1.

The deletion in the amino terminal of hst-1 is preferred.

When causing a deletion in the amino terminal, the codon for the gene that encodes the carboxyl terminal of the amino acid sequence to be eliminated is changed to the Met-encoding ATG codon by site-directed mutagenesis, and an appropriate restriction enzyme recognition site is created on the 5'-terminal side of the ATG codon to facilitate promoter ligation, or an oligonucleotide having ATG is ligated to a gene having a deletion in the amino terminal, as caused via restriction enzyme with reading frame justification.

When causing a deletion in the middle portion of the amino acid sequence, a unique restriction enzyme recognition site is created on both the 5'- and 3'-terminal sides of the gene that encodes the sequence to be deleted by site-directed mutagenesis; these sites are digested with enzyme and the resulting fragment is extracted, followed by gene religation to yield a gene that encodes the desired hst-1 lacking amino acid residues. Of course, reading frame discrepancy due to digestion with restriction enzyme must be avoided.

When inducing a deletion in the carboxyl terminal of the amino acid sequence, the codon for the gene that encodes the amino acids on the amino terminal side of the sequence to be eliminated is changed to a stop codon by site-directed mutagenesis.

The deletion type mutein of the present invention may lack a number of constituent amino acids of hst-1 and also have at least one of the constituent amino acids replaced by another amino acid.

Examples of constituent amino acids which may be replaced to obtain the muteins of the present invention include cysteine and non-cysteine amino acids (e.g., aspartic acid, arginine).

When the constituent amino acid to be replaced is cysteine, it is preferable that the replacing amino acid be a neutral amino acid, for instance. Example neutral amino acids include glycine, valine, alanine, leucine, isoleucine, tyrosine, phenylalanine, histidine, tryptophan, serine, threonine and methionine, with preference given to serine and threonine.

When the constituent amino acid to be replaced is a non-cysteine amino acid, the selected replacing amino acid should be different from the constituent amino acid with respect to amino acid hydrophilicity, hydrophobicity or electric charge. Specifically, when the constituent amino acid to be replaced is aspartic acid, example replacing amino acids include asparagine, threonine, valine, phenylalanine and arginine, with preference given to asparagine and arginine.

When the constituent amino acid to be replaced is arginine, example replacing amino acids include glutamine, threonine, leucine, phenylalanine and aspartic acid, with preference given to glutamine.

It should be noted that when the deletion type hst-1 mutein of the present invention is produced by site-directed mutagenesis, a number of mutations may be induced in the DNA sequence; i.e., the DNA codon corresponding to the amino acid involves degeneracy.

For example, when a gene coding for the present mutein is prepared for the purpose of obtaining a mutein wherein a non-cysteine constituent amino acid has been replaced by another amino acid, an oligonucleotide primer is used to change the codon, as in the case of cysteine.

It should be noted, however, that the design of the oligonucleotide primer varies, depending on which amino acid is changed.

The primer is hybridized to a single-stranded phage such as M13, the cloned single strand of the hst-1 gene, [Yanisch-Perror, C., Vieira, J. Messing: Gene, 33, 103–119 (1985): Messing, J.: Methods in Enzymology, 101, 20–78 (1983)], fd [R. Herrman et al.: Molecular and General Genetics, 177, 231 (1980)] or Φ×174 [M. Smith and S. Gillam: Genetic Engineering, Plenum Press, vol. 3, pp. 1–32 (1981)]. It is recognized that the phage is capable of carrying either the sense or antisense chain of the gene. When the phage carries the antisense chain, the primer may not be identical to the sense chain region containing the codon to be mutated, due to codon degeneracy, and there may be a discrepancy from the codon that determines the triplet that encodes another amino acid. Similarly, when the phage carries the sense chain, the primer may not be complementary to the sense chain region containing the codon to be mutated, except for the appropriate discrepancy in the triplet that makes a pair with the codon to be eliminated. The conditions of hybridization are described by M. Smith and S. Gillam (mentioned above). Temperature is normally 0° to 70° C., more specifically 10° to 50° C. After hybridization, the primer is elongated on the phage DNA by reaction with *Escherichia coli* DNA polymerase I, T4 DNA polymerase, reverse transcriptase or another appropriate DNA polymerase. The resulting dsDNA is converted to cyclized dsDNA by treatment with a DNA ligase such as T4 DNA ligase. A DNA molecule containing the single-stranded region can be disrupted by S1 endonuclease treatment.

The resulting mutagenic heteroduplex is used to transform an infectable host organism or cell. In replication of the heteroduplex with the host, offspring are yielded from both chains. Following replication, the mutant gene is isolated from an offspring of the chain of the mutant and inserted into an appropriate vector. This vector is used to transform an appropriate host organism or cell.

The phage DNA carrying the mutated gene is then isolated and integrated in a plasmid.

Examples of the plasmid to which DNA is integrated include *Escherichia coli*-derived plasmids such as pBR322 [Gene, 2, 95 (1977)], pBR325 [Gene, 4, 121 (1978)], pUC12 [Gene, 19, 259 (1982)] and pUC13 [Gene, 19, 259 (1982)] and *Bacillus subtilis*-derived plasmids such as pUB110 [Biochemical and Biophysical Research Communication, 112, 678 (1983)], but any other plasmid can be used, as long as it is replicable and retainable in the host.

Examples of the method of insertion into the plasmid include the method described by T. Maniatis et al. in Molecular Cloning, Cold Spring Harbor Laboratory, p. 239 (1982).

The cloned gene can be ligated to any vehicle (vector) suitable for its expression at a site downstream from the promoter present therein, to yield an expression vector.

Example vehicles (vector) for recombinant vector preparation include *Escherichia coli*-derived plasmids such as pBR322 [Gene, 2, 95 (1977)], pBR325 [Gene, 4, 121 (1978)], pUC12 [Gene, 19, 259 (1982)] and pUC13 [Gene, 19, 259 (1982)], *Bacillus subtilis*-derived plasmids such as pUB110 [Biochemical and Biophysical Research Communication, 112, 6678 (1983)], pTP5 and pC194, yeast-derived plasmids (e.g. pSH19, pSH15), bacteriophages such as λ phage, and animal viruses such as retrovirus and vacinia virus.

The gene described above may have a translation initiation codon ATG at its 5'-terminal and a translation termination codon TAA, TGA or TAG at its 3'-terminal. To express the gene, a promoter is ligated thereto, upstream. Any promoter can be used for the present invention, as long as it suits the host used for gene expression.

Examples of preferable promoters include trp promoter, lac promoter, rec A promoter, λpL promoter, lpp promoter and T7 promoter, when the transformation host is a bacterium of the genus Escherichia; SPO1 promoter, SPO2 promoter and penP promoter, when the transformation host is a bacterium of the genus Bacillus; and PHO5 promoter, PGK promoter, GAP promoter and ADH promoter, when the transformation host is a yeast, with particular preference given to a combination of a bacterium of the genus Escherichia as the host and trp promoter or T7 promoter.

When the host is an animal cell, examples of preferable promoters include SV40-derived promoter and retrovirus promoter, with particular preference given to SV40-derived promoter.

The DNA-containing vector thus constructed is used to prepare a transformat.

Example hosts include bacteria of the genus Escherichia, bacteria of the genus Bacillus, yeast and animal cells.

Example bacteria of the genus Escherichia described above include *Escherichia coli* strains K12DH1 [Proc. Natl. Acad. Sci. USA, 60, 160 (1968)], M103 [Nucleic Acids Research, 9, 309 (1981)], JA221 [Journal of Molecular Biology, 120, 517 (1978)], HB101 [Journal of Molecular Biology, 41, 459 (1969)] and C600 [Genetics, 39, 440 (1954)].

Example bacteria of the genus Bacillus described above include *Bacillus subtilis* strains MI114 [Gene, 24, 255 (1983)] and 207-21 [Journal of Biochemistry, 95, 87 (1984)].

Examples of the yeasts described above include *Saccharomyces cerevisiae* strains AH22R-, NA87-11A and DKD-5D.

The animal cell described above is preferably of an established cell line. Examples of such cells include simian COS-7 cells [Cell, 23, 157 (1981)], Vero, Chinese hamster CHO cells, mouse L cells and human FL cells.

The bacteria of the genus Escherichia described above are transformed in accordance with, for example, the methods described in Proc. Natl. Acad. Sci. USA, 69, 2110 (1972) and Gene, 17, 107 (1982).

A bacterium of the genus Bacillus is transformed in accordance with, for example, the method described in Molecular and General Genetics, 168, 111 (1979).

A yeast is transformed in accordance with, for example, the method described in Proc. Natl. Acad. Sci. USA, 75, 1929 (1978).

An animal cell is transformed in accordance with, for example, the method described in Virology, 52, 456 (1973).

A transformant transformed with a vector containing a cDNA which codes for the present mutein is thus obtained.

When cultivating a transformant whose host is a bacterium of the genus Escherichia or Bacillus, it is appropriate to use a liquid medium, formulated with carbon sources, nitrogen sources and inorganic and other substances essential to the growth of the transformant. Example carbon sources include glucose, dextrin, soluble starch and sucrose. Example nitrogen sources include inorganic or organic substances such as ammonium salts, nitrates, corn steep liquor, peptone, caseine, meat extracts, soybean flower and potato extracts. Example iorganic substances include calcium chloride, sodium dihydrogen phosphate and magnesium chloride. Yeast extracts, vitamins, growth promoters and other substances may also be added.

It is desirable that the pH of the medium be about 6 to 8.

Example of preferable media for cultivation of a bacterium of the genus Escherichia include an M9 medium containing glucose and casamino acid [Miller: Journal of Experiments in Molecular Genetics, 431–433, Cold Spring Harbor Laboratory, New York (1972)]. To increase promoter efficiency as desired, an agent such as 3β-indolylacrylic acid may be added.

When the host is a bacterium of the genus Escherichia, cultivation is normally carried out at 15° to 43° C. for 3 to 24 hours, with aeration and stirring if necessary.

When the host is a bacterium of the genus Bacillus, cultivation is normally carried out at 30° to 40° C. for 6 to 24 hours, with aeration and stirring if necessary.

When cultivating a transformant whose host is a yeast, example usable media include Burkholder's minimal medium [Bostian, K. L. et al.: Proc. Natl. Acad. Sci. USA, 77, 4505 (1980)]. It is preferable to adjust the medium to a pH of 5 to 8. Cultivation is normally carried out at 20° to 35° C. for 24 to 72 hours, with aeration and stirring if necessary.

When cultivating a transformant whose host is an animal cell, example usable media include MEM medium [Science, 122, 501 (1952)], DMEM medium [Virology, 8, 396 (1959)], RPMI1640 medium [Journal of the American Medical Association, 199, 519 (1967)] and 199 medium [Proceedings of the Society for the Biological Medicine, 73, 1 (1950)]. The medium may be formulated with 5 to 20% fetal bovine serum. It is preferable that the pH be about 6 to 8. Cultivation is normally carried out at 30° to 40° C. for 15 to 60 hours, with aeration and stirring if necessary.

The present mutein can be separated and purified from the culture described above by, for example, the following method.

Methods of extracting the present mutein from cultured bacterial or other cells include that in which bacterial or other cells, collected by a known method after cultivation, are suspended in a buffer containing a protein denaturant such as guanidine chloride. This is followed by extracellular elution of the desired protein, and a procedure by which bacterial or other cells are disrupted by French press, ultrasonication, lysozyme treatment and/or freeze-thawing and then centrifuged to yield a deletion type hst-1 mutein, with preference given to the method using lysozyme and ultrasonication in combination.

In purifying the present mutein from the supernatant thus obtained, separation/purification methods known per se can be carried out in combination. Such methods include those based on solubility, such as salting-out and solvent precipitation; those based on molecular weight differences, such as dialysis, ultrafiltration, gel filtration and SDS-polyacrylamide gel electrophoresis; those based on electric charge differences, such as ion exchange chromatography; those based on specific affinity, such as affinity chromatography; those based on hydrophobicity differences, such as reverse phase high performance liquid chromatography; and those based on isoelectric point differences, such as isoelectric focusing.

More specifically, contaminant nucleic acids, acidic proteins and other mingling substances can be removed by applying the supernatant described above to ion exchange chromatography using DEAE cellulose or another substance as a carrier. For example, it is efficient to apply the supernatant to a DEAE cellulose column equilibrated with a buffer such as nearly neutral Tris, and collect the effluent fraction. Also, it is possible to purify the present mutein via carrier adsorption by applying the supernatant described above to ion exchange chromatography using CM cellulose or another carrier and eluting it with a salt solution.

The present mutein can be purified directly from the bacterial cell extract by column chromatography using an acidic resin such as CM Sephadex. For example, efficient purification is possible by applying the supernatant to a CM-cellulose column equilibrated with a weakly acidic buffer (e.g. phosphate buffer). The present mutein can be eluted by washing the column with the same buffer as above and then eluting the column with a buffer containing a salt (e.g. NaCl). The resulting eluated may be lyophilized after dialysis.

It is advantageous to apply affinity chromatography, using heparin-Sepharose as a carrier, to the present mutein in *Escherichia coli* extract to purify the present mutein. For example, the present mutein can be purified by applying the eluate described above to a heparin-Sepharose column equilibrated with a nearly neutral buffer such as Tris or phosphate buffer, washing the column thoroughly, and then carrying out linear gradient elution with NaCl etc.

Heparin columns developed specially for high performance liquid chromatography (e.g. Shodex AF-pak HR 894, produced by Showa Denko, KK) serve well for this purpose.

Like the heparin-Sepharose column described above, this heparin column makes it possible to recover the present mutein as an almost uniform authentic preparation by applying the sample to the column equilibrated with a nearly neutral buffer, washing the sample thoroughly and then carrying out elution on a linear density gradient of NaCl etc.

The authentic preparation thus obtained may be dialyzed and lyophilized to a dry powder. Also, it is preferable to store it in the presence of serum albumin etc., added as a carrier to prevent adsorption of the authentic preparation to the container.

Also preferable is the presence of a trace amount of reducing agent during purification or storage, which serves well to prevent oxidation of the authentic preparation. Examples of the reducing agent include β-mercaptoethanol, dithiothreitol and glutathione.

A substantially pure deletion type mutein of hst-1 is thus obtained, which is substantially free of pyrogen and endotoxin. The substantially pure deletion type mutein of hst-1 of the present invention preferably has a protein content of not less than 95% (w/w), more preferably not less than 98% (w/w). This polypeptide may have Met at its N-terminal.

The activity of the resulting deletion type mutein of hst-1 can be determined on the basis of the growth-promoting effect of BALBA/c3T3 cells, and other indexes.

Transfection or transformation with the DNA of the present invention permits mass-production of deletion type mutein of hst-1 even in various kinds of cells which are essentially capable of synthesizing only a very small amount of deletion type mutein of hst-1 or totally uncapable of synthesizing it, with efficient induction of deletion type mutein of hst-1.

Since an expression plasmid containing the gene that encodes the deletion type mutein of hst-1 of the present invention, when introduced into various cells, enables them to produce the deletion type mutein of hst-1, it permits the production of the deletion type mutein of hst-1 in large amounts.

Since the deletion type mutein of hst-1 thus produced possesses growth-promoting effects on vascular endothelial and other cells, has angiogenesis-promoting effects and is low in toxicity, it can be used as a therapeutic drug such as a healing promoter for burns, wounds, surgical injuries etc. It can also be used as a reagent for promoting cell cultivation.

When the deletion type mutein of hst-1 of the present invention is used as a pharmaceutical, it can be safely administered orally or parenterally, singly in the form of bulk powder or in combination with a pharmacologically acceptable carrier, excipient or diluent in the form of a pharmaceutical composition (e.g., injections, tablets, capsules, solutions, ointments) to warm-blooded mammal (e.g., humans, mice, rats, hamsters, rabbits, dogs, cats).

An injection is prepared in accordance with a standard method using physiological saline or an aqueous solution containing glucose or other auxiliaries. Other pharmaceutical compositions such as tablets and capsules can also be prepared in accordance with standard methods. In preparing injections, solutions, tablets, capsules etc. as pharmaceutical compositions, the process is carried out under aseptic conditions.

When using the deletion type mutein of hst-1 of the present invention as a pharmaceutical as described above, it is administered, for instance, to a warm-blooded animal mentioned above at an appropriate dose chosen from the range of from about 1 ng to 100 μg/kg body weight daily, in view of the route of administration, symptoms, and other aspects.

When using the deletion type mutein of hst-1 of the present invention as a reagent for the promotion of cell cultivation, it is preferable to add it to the medium so that its final concentration becomes 0.01 to 10 μg, more preferably 0.1 to 10 μg, per liter medium.

Since the present mutein possesses high healing-promoting activities on damaged living tissue, it can serve well as a therapeutic medicine such as a healing promoter for burns, wounds etc.

As the present mutein has an excellent cell growth promoting activity and is stable under acidic conditions, the present mutein can be used as a therapeutical medicine for treating ulcers such as gastrointestinal tract ulcers.

BRIEF EXPLANATION OF THE DRAWINGS

FIG. 1 shows the amino acid sequence of mature hst-1.

FIG. 2 shows the amino acid sequence deduced from the hst-1 coding region containing a leader sequence, which onstitutes the open reading frame of hst-1 cDNA.

FIG. 3 shows the amino acid sequence of hst-1 mutein N27 obtained in Example 1.

FIG. 8 shows another pattern on SDS-PAGE, obtained in Example 1.

FIG. 10 shows the results of determination of the DNA synthesis-inducing activity on mouse BALB/c3T3 cells, obtained in Example 6.

FIG. 12 shows the residual activity under acidic conditions, obtained in Example 10.

FIG. 13 shows the results of the effect of hst-1 mutein N27 on the binding of radiolabeled rhbFGF, obtained in Example 10.

The abbreviations for bases and amino acids used in the present specification and the attached drawings are based on the abbreviations specified by the IUPAC-IUB Commission on Biochemical Nomenclature or those which are commonly used in relevant fields. Examples are given below. It should be noted that when there is a possibility that an optical isomer is present in any amino acid, it is an L-body unless otherwise stated.

| | |
|---|---|
| DNA | Deoxyribonucleic acid |
| cDNA | Complementary deoxyribonucleic acid |
| A | Adenine |
| T | Thymine |
| G | Guanine |
| C | Cytosine |
| RNA | Ribonucleic acid |
| dATP | Deoxyadenosine triphosphate |
| dTTP | Deoxythymidine triphosphate |
| dGTP | Deoxyguanosine triphosphate |
| dCTP | Deoxycytidine triphosphate |
| ATP | Adenosine triphosphate |
| Tdr | Thymidine |
| EDTA | Ethylenediaminetetraacetic acid |
| SDS | Sodium dodecyl sulfate |
| Gly | Glycine |
| Ala | Alanine |
| Val | Valine |
| Leu | Leucine |
| Ile | Isoleucine |
| Ser | Serine |
| Thr | Threonine |
| Cys | Cysteine |
| Met | Methionine |
| Glu | Glutamic acid |
| Asp | Aspartic acid |
| Lys | Lysine |
| Arg | Arginine |
| His | Histidine |
| Phe | Phenylalanine |
| Tyr | Tyrosine |
| Trp | Tryptophan |
| Pro | Proline |
| Asn | Asparagine |
| Gln | Glutamine |

The transformant obtained in Examples given below has been deposited at the Institute for Fermentation, Osaka, Japan and also at the Fermentation Research Institute, Agency of Industrial Science and Technology, Ministry of International Trade and Industry, Japan, under the Budapest Treaty. The accession numbers and dates of accession are listed in the following Table 1.

TABLE 1

| Transformant | IFO | FRI |
|---|---|---|
| E. coli MM294(DE3)/ pLysS, pTB1051 [Example 1 (b)] | IFO 14952 (September 27, 1989) | FERM BP-2621 (October 4, 1989) |

The mutein obtained in the following Example 1 is a mutein lacking N-terminal amino acids Nos. 1 through 27,

11 and it is referred to as hst-1 mutein N27. The amino acid sequence of hst-1 mutein N27 is shown in FIG. 3.

The present invention is hereinafter described in more detail by means of the following examples, but the invention is by no means limited by them.

EXAMPLE 1 a) Construction of expression plasmid

Figure 4:
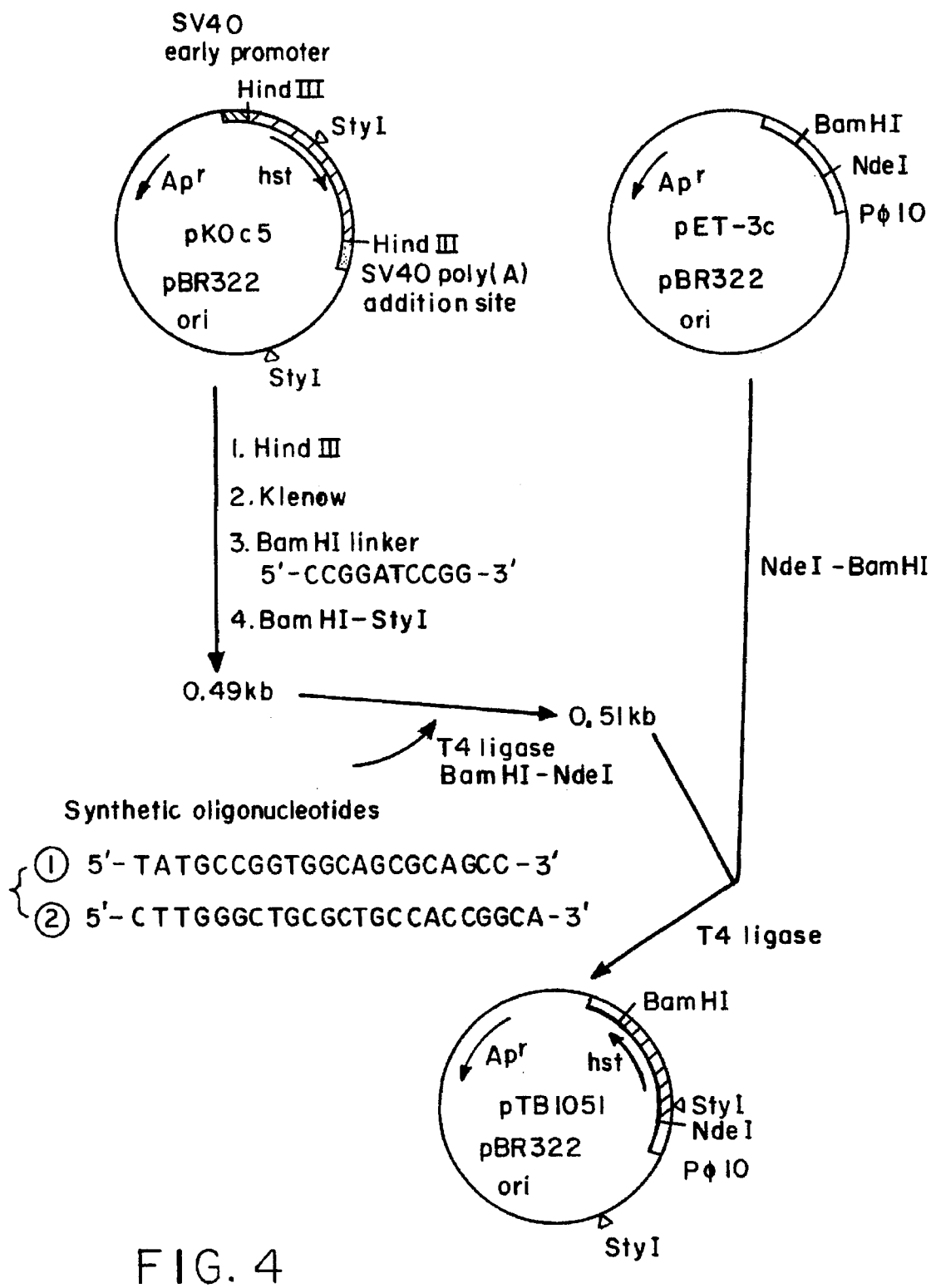
FIG. 4 shows the construction scheme of the plasmid pTB1051 obtained in Example 1.

Plasmid pKOc5 [Proc. Natl. Acad. Sci. USA, 84,2980–2984 (1987)], which harbors a human hst-1 cDNA, was cleaved with Hind III and blunted by Klenow fragment reaction with E. coli DNA polymerase I. After being ligated with a Bam HI linker by T4 ligase reaction, the fragment was cleaved with Bam HI-Sty I to yield a 0.49 kb DNA fragment. Synthetic oligonucleotides 5'TATGCCGGTGGCAGCGCAGCC3'and 5'CTTGGGCTGCGCTGCCACCGGCA3'were ligated to the 0.49 kb DNA fragment obtained above the 5'-terminal side to yield a 0.51 kb Nde I-Bam HI DNA fragment (containing an initiation codon ATG and human hst-1 cDNA nucleotide Nos. 413 through 916), which was then inserted into E. coli expression vector pET3c, harboring T7 phage Φ10 promoter [Gene, 56, 125–135 (1987)] between the Nde I-Bam HI sites to yield pTB1051 (FIG. 4).

b) Expression of cDNA in E. coli

A phage DE3 [Studier, F. W. et al.: J. Mol. Biol., 189, 113–130 (1986)] having the RNA polymerase gene of T7 phage was lysogenized to E. coli MM294 strain, followed by introduction of plasmid pLysS [Studier, F. W. et al.: J. Mol. Biol., 189, 113–130 (1986)], harboring the lysozyme gene of T7 phage, to yield E. coli MM294(DE3)/pLysS strain.

The plasmid pTB1051 obtained in (a) above was introduced into this E. coli MM294(DE3)/pLysS strain to yield E. coli MM294(DE3)/pLysS,pTB1051 (IFO 14952, FERM BP-2621). This strain was cultivated in an L medium containing 10 μg/ml chloramphenicol and 35 μg/ml ampicillin. When the klett value reached about 120, isopropyl β-D-thiogalactopyranoside (IPTG) was added to achieve a final concentration of 0.4 mM, followed by cultivation for 4 more hours. Bacterial cells were collected via centrifugation, washed with ice-cooled phosphate-buffered saline (PBS), and recollected and stored at −20° C. until use.

c) Purification of recombinant hst-1 mutein

Bacterial cells collected from the 10-liter culture were suspended in 250 ml of an ice-cooled solution containing 10 mM Tris-HCl (pH 7.4), 10 mM EDTA, 0.5 M NaCl, 10% sucrose and 1 mM PMSF, followed by the addition of egg white lysozyme to achieve a final concentration of 0.5 mg/ml. After being kept standing under ice-cooling conditions for 1 hour, this suspension was incubated at 37° C. for 5 minutes, followed by ultrasonication (20 seconds×2 times) with ice cooling and then centrifugation (SORVALL, 18 Krpm, 30 minutes, 4° C.) to yield a supernatant for a bacterial cell extract.

250 ml of this bacterial cell extract was passed through a column (5 cm dia.×5 cm) of Q-Sepharose (Pharmacia) equilibrated with a solution of 20 mM Tris-HCl (pH 7.6) and 0.5M NaCl to remove the nucleic acid components. The effluent from the column and the column washings, with a solution of 20 mM Tris-HCl (pH 7.6) and 0.5M NaCl, were combined (Q-Sepharose effluent fraction 450 ml). This fraction was applied to a high performance liquid chromatograph (Gilson Co.) equipped with a heparin column Shodex AF-pak HR-2094 (2 cm ID×25 cm, produced by Showa Denko, KK). After column washing by sequential additions of a 20 mM Tris-HCl solution (pH 7.6) and a solution of 20 mM Tris-HCl (pH 7.6) and 0.5M NaCl, linear gradient elution was conducted on a density gradient of 0.5M to 2M NaCl in a 20 mM Tris-HCl buffer (pH 7.6) at a flow rate of 6.0 ml/min for 180 minutes.

Figure 5:
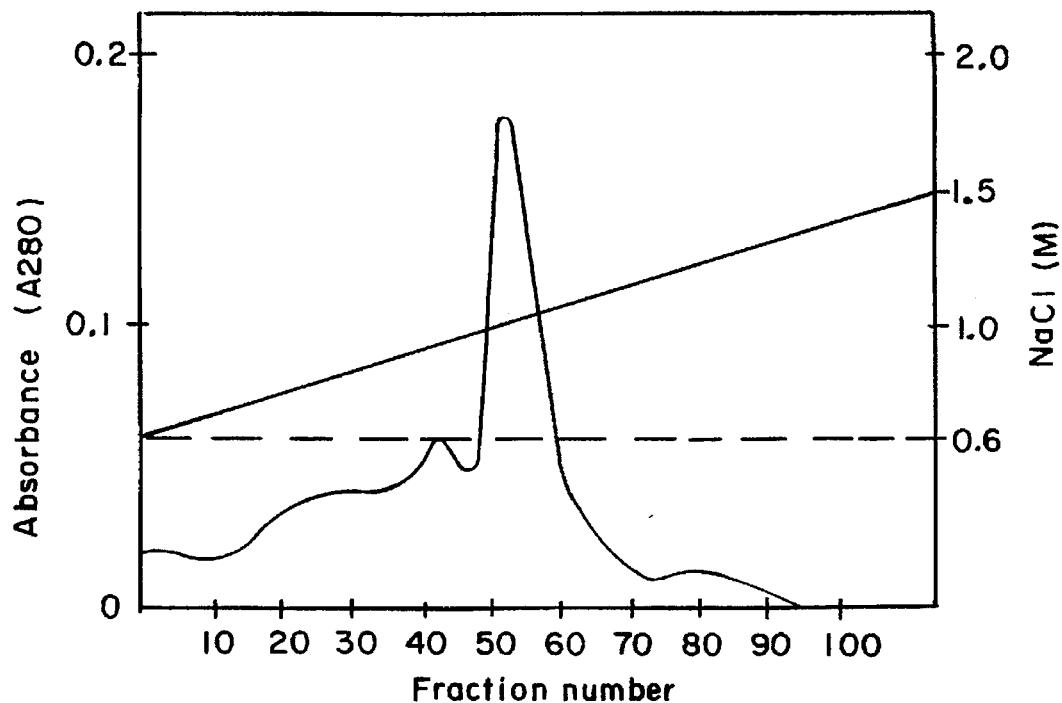
FIG. 5 shows an elution pattern obtained in Example 1.
Figure 6:
FIG. 6 shows a pattern on SDS-PAGE, obtained in Example 1.

In the elution pattern shown in FIG. 5, the ordinate indicates absorbance at $OD_{280}$ and NaCl concentration gradient, the abscissa indicates fraction number. Gradient elution was initiated at time 0 point. Fraction was taken every 0.75 minutes. The protein specific activity of these fractions and quantitative hst-1 mutein recovery are shown in Table 2. The SDS-PAGE (12.5% polyacrylamide gel) patterns of respective fractions, each showing a peak, are shown in FIG. 6.

TABLE 2

|  | Protein content (mg) | hst-1 activity (as mg bFGF) |
| --- | --- | --- |
| Crude extract | 2530 | 3.8 |
| Q-Sepharose effluent fraction | 2240 | 5.2 |
| Heparin column elution fraction (47–60) | 6.5 | — |

—: Not measured.

d) Reverse phase C4 HPLC

Figure 7:
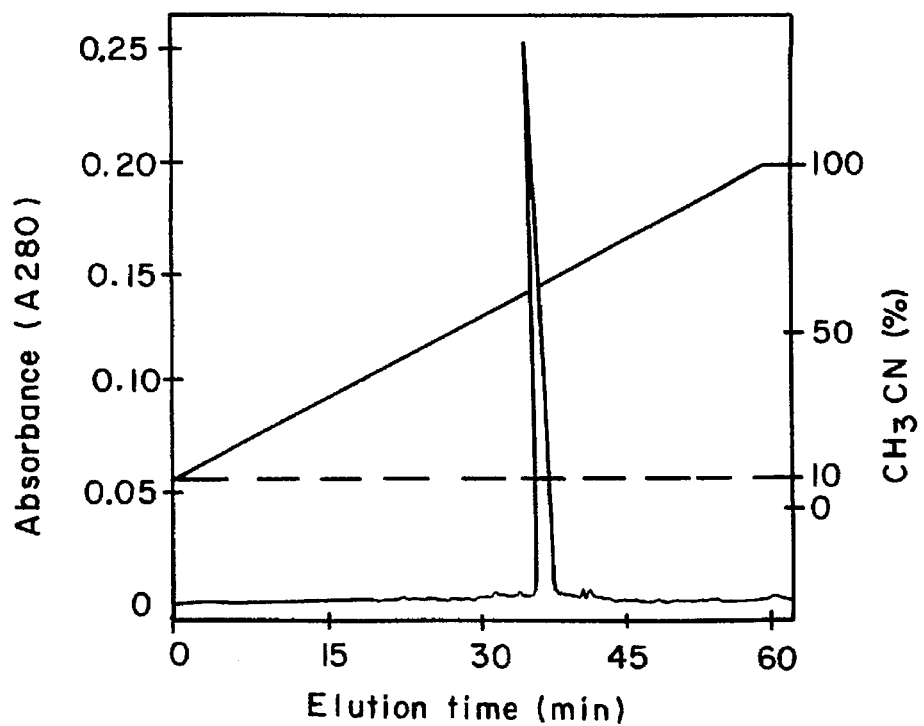
FIG. 7 shows another elution pattern, obtained in Example 1.
Figure 8:
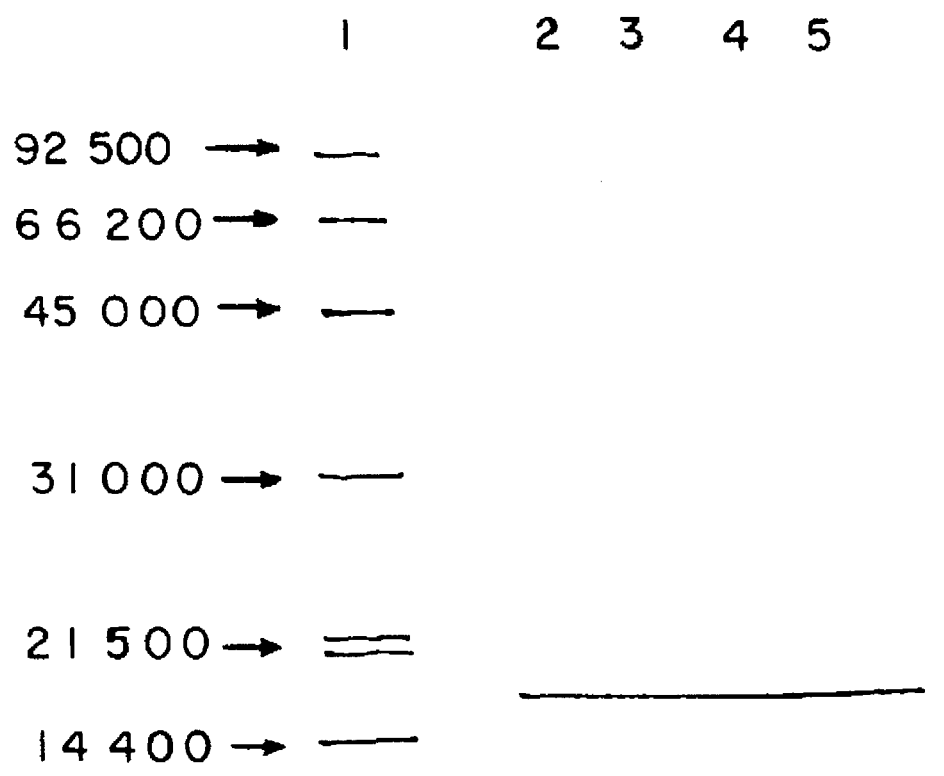

About half (300 μg protein) of the elution fraction No. 56 from the heparin HPLC column was applied to a reverse phase C4 column (VYDAC) and eluted on a linear gradient of 0 to 90% acetonitrile in the presence of 0.1% TFA at a flow rate of 1 ml/min for a gradation time of 60 minutes, the elution pattern was then examined (FIG. 7). The SDS-PAGE (12.5% polyacrylamide gel) pattern of the peak fraction detected at 36 to 37 minutes, together with that of elution fraction No. 56 from the heparin column, is shown in FIG. 8.

In FIG. 8, 1 through 5 show the 12.5% polyacrylamide gel patterns of the molecular weight marker (50 ng), fraction No. 56 (50 ng) eluted from the heparin HPLC column, fraction No. 56 (100 ng) eluted from the heparin HPLC column, reverse phase HPLC elution fraction (50 ng) and reverse phase HPLC elution fraction (100 ng), respectively. These proteins were found to have a specific activity of 0.43, relative to that of recombinant human bFGF (rhbFGF) (European Patent Publication No. 237,966), taken as 1.00. Changes in specific activity and hst-1 mutein N27 recovery rate in the purification process and are shown in Table 3, with the specific activity of bovine pituitary FGF (produced by Takara Shuzo) taken as 1.

hst-1 mutein N27 was thus obtained, which has the amino acid sequence shown in FIG. 3.

TABLE 3

|  | Protein content (mg) | Specific activity | Recovery rate (%) |
| --- | --- | --- | --- |
| Bacterial cell crude extract | 2530 | 0.013 | 100 |
| Q-Sepharose effluent fraction | 2152 | 0.014 | 91 |
| Heparin column elution fraction | 11 | 0.54 | 18 | e) Biological activities hst-1 mutein activity was determined in accordance with the method of Sasada et al. [Sasada et al.: Mol. Cell Biol., 8,588–594 (1988)] with the uptake of [$^3$H] thymidine measured as an index of induction of DNA synthesis in mouse BALB/c3T3 cells. The results are shown in Table 2 above.

EXAMPLE 2

(Promotion of Vascular Endothelial Cell Growth)

The hst-1 mutein N27 obtained in Example 1 was assayed for effect on cell growth as follows: The cells used in this assay were venous endothelial cells isolated from human umbilical cord (hereinafter referred to as HUVE cells). Cell growth rate was determined by the MTT assay method described below, with slight modification to the method of Tada et al. [Journal of Immunological Methods, 93, 157 (1986)]. Subcultured HUVE cells were dissociated to single cells using a 0.125% trypsin enzyme solution (produced by Boehringer Manheim Co.) containing 0.002% EDTA (produced by Dojin Kagaku K.K. Japan, 345-01882). The resulting single cells were suspended in an HUVE cell culture medium comprising GIT medium (produced by Nippon Seiyaku, 398-00515) and 2.5% fetal bovine serum (produced by Whittaker Bioproduct Co.). After counting the cells present in this suspension using a Coulter cell counter (Coulter Co., ZM model), the cells were cultivated as follows: A 100 µl portion of the HUVE cell suspension, containing $2\times10^3$ HUVE cells, was seeded to a 96-well culture plate (Nunc Co., F96) and incubated at 37° C. (Hitachi carbon dioxide-nitrogen gas control incubator CH-16 model, 5% $CO_2$,7% $O_2$). The day after incubation, the samples described below were prepared with HUVE cell culture medium. A 100 µl portion of each sample was added to the HUVE cells cultivated on the 96-well culture plate. The assay subject samples were prepared with 1) hst-1 mutein N27 alone to achieve a final concentration of 0.004 ng/ml to 2.0 ng/ml, or 2) the hst-1 mutein N27 described above in combination with heparin (produced by Sigma Co.) was added to achieve a final concentration of 5.0 µg/ml. After each sample was added, incubation was carried out for 3 more days, when the medium was removed from the culture plate, and 100 µl of HUVE medium containing 1.0 mg/ml MTT reagent (produced by Dojin Kagaku, 34101823) was added, followed by incubation at 37° C. for 4 hours. 100 µl of a 10% aqueous solution of SDS (produced by Wako Pure Chemical, 191-07145) was then added, followed by incubation at 37° C. for 4 hours. After completion of the reaction, the 96-well culture plate containing the reaction mixture was shaken and the reaction mixture absorbance was determined at a wavelength of 590 nm, using a microtiter plate absorptiometer (produced by Titertech Co., MCC341). The results are shown in FIG. 9.

Figure 9:
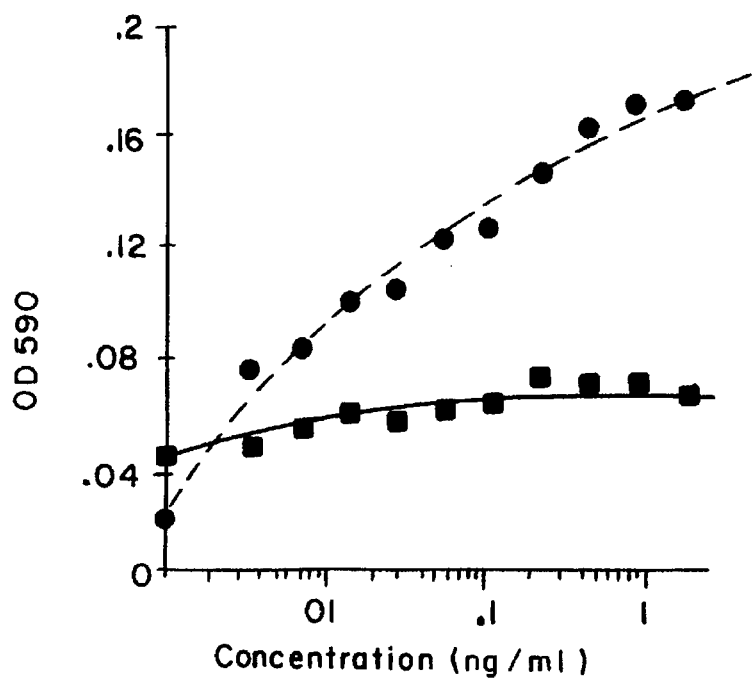
FIG. 9 shows the results of the cell growth-promoting effect of hst-1 mutein N27 on human vascular endothelial cells, obtained in Example 2.

In FIG. 9, the abscissa indicates the concentration of hst-1 mutein N27 added to the culture medium of vascular endothelial cells, the ordinate indicating the absorbance of reaction product solution in SDS, determined at a wavelength of 590 nm after reaction with MTT reagent following completion of cultivation, the absorbance corresponding to the amount of cells. Solid line ■ shows the results obtained when hst-1 mutein N27 alone was added, dotted line ● shows the results obtained when hst-1 mutein N27 was added together with 5.0 µg/ml of heparin. As seen in FIG. 9, in the concentration range examined, hst-1 mutein N27 alone did not show a cell growth-promoting effect on HUVE cells, but in the presence of 5.0 µg/ml heparin, it did promote such growth.

EXAMPLE 3

(CAM Assay)

The hst-1 mutein N27 obtained in Example 1 was subjected to CAM (chorioallantoic membrane) assay by the method of Auerbach [Developmental Biology, 41,391 (1974)] with slight modification. After a fertilized chick egg was incubated in an incubator at 37° C. for 3 days, the egg shell was removed, followed by incubation at 37° C. for 1 week (Napco carbon dioxide incubator 6300, 0% $CO_2$, $H_2O$ saturated). Onto a polypropylene disc having a diameter of 6 mm, was spotted varying concentrations of hst-1 mutein N27 solution (prepared by dissolving hst-1 mutein N27 in a buffer comprising 20 mM Tris-HCl, pH 7.4, and 1.0M NaCl) in an amount of 200 ng or 50 ng. After being air-dried in a laminar flow bench, this disc was placed on a chick embryo chorioallantoic membrane (CAM) and incubated at 37° C. for 3 days, and the status of angiogenesis was observed. Also, 10 µg of an aqueous solution of heparin (produced by Sigma Co.) containing hst-1 mutein N27 and, as a control, a solution containing not hst-1 mutein N27 but the same amount of bovine serum albumin (produced by Sigma Co.) were each spotted on another disc. After being air-dried in the same manner as above, each disc was placed on a chick embryo chorioallantoic membrane and incubated. The results are shown in Table 4. In the presence of 200 ng of hst-1 mutein N27 alone, angiogenesis occurred. When heparin was used in combination, angiogenesis occurred in the presence of 50 ng of hst-1 mutein N27 as well as 200 ng. However, almost no angiogenesis occurred in the presence of the buffer alone or heparin alone.

TABLE 4

| Positive Value Ratio in CAM Assay (Number of Positive Samples/Number of Measured Samples) | | |
|---|---|---|
| | Amount of hst-1 mutein N27 or bovine serum albumin (ng) | |
| Sample | 200 | 50 |
| hst-1 mutein N27 | 8/12 | 2/12 |
| Bovine serum albumin | 0/12 | 0/12 |
| hst-1 mutein N27 + heparin | 9/12 | 6/12 |
| Bovine serum albumin + heparin | 1/12 | 1/12 |

EXAMPLE 4

(Amino Acid Composition)

The purified hst-1 mutein N27 protein obtained in Example 1-d) (14 µg) was transferred to a glass test tube for hydrolysis. After a 200-fold amount (v/w) of constant boiling point hydrochloric acid containing 4% thioglycolic acid was added, this test tube was sealed under reduced pressure, followed by hydrolysis at 110° C. for 24 hours. After hydrolysis, the tube was opened, and the hydrochloric acid was evaporated off under reduced pressure. The residue was dissolved in 0.02N hydrochloric acid and subjected to amino acid analysis using a Hitachi 835 high performance amino acid analyzer. Neither cystine nor cysteine was included in the analysis. The residues of each amino acid were counted. The results are shown in Table 5.

The numbers of amino acid residues shown in Table 5 agree very well with the amino acid composition of hst-1 mutein N27 deduced from the base sequence of its cDNA.

TABLE 5

| | Number of amino acid residues per molecule | |
|---|---|---|
| Amino acid | Found value for hst-1 mutein N27 | Theoretical value of amino acid content in hst-1 mutein N27 deduced from the base sequence of the cDNA |
| Asp/Asn | 11.6 | 11 |
| Glu/Gln | 10.3 | 9 |
| Ser | 10.8 | 11 |
| Gly | 15.5 | 15 |
| His | 3.4 | 3 |
| Arg | 10.1 | 9 |
| Thr | 6.0 | 6 |
| Ala | 12 | 12 |
| Pro | 9.5 | 9 |
| Tyr | 5.8 | 7 |
| Val | 9.2 | 10 |
| Met | 2.7 | 4 |
| H-Cys | — | 2 |
| Ile | 5.7 | 6 |
| Leu | 14.4 | 15 |
| Phe | 8.3 | 9 |
| Trp | — | 0 |
| Lys | 9.5 | 11 |

EXAMPLE 5

(Amino-terminal Amino Acid Sequence and Carboxyl-terminal Amino Acid Residues)

A 28 µg portion of the purified hst-1 mutein N27 protein obtained in Example 1-d) was subjected to N-terminal amino acid sequencing using a gas phase protein sequencer (produced by Applied Biosystems Inc., model 470A). The resulting phenylthiohydantoin-amino acid (PTH-amino acid) was identified and quantitated using a high performance liquid chromatograph produced by Varian. The results are shown in Table 6. As is evident from these results, the amino-terminal amino acid sequence of hst-1 mutein N27 exactly agrees with the expected sequence deduced from the base sequence of the DNA of the expression plasmid. It was also found that the methionine derived from the translation initiation codon has been removed.

Also, the amino acid residues in the carboxyl terminal were examined by the hydrazinolysis method. As expected, leucine was detected in the cDNA sequence.

TABLE 6

| | PTH amino acid | |
|---|---|---|
| Cycle | Amino acid residue | p mol |
| 1 | Pro | 348 |
| 2 | Val | 345 |
| 3 | Ala | 409 |
| 4 | Ala | 418 |
| 5 | Gln | 321 |
| 6 | Pro | 236 |
| 7 | Lys | 211 |
| 8 | Glu | 172 |
| 9 | Ala | 216 |
| 10 | Ala | 320 |
| 11 | Val | 177 |
| 12 | Gln | 153 |
| 13 | Ser | 38 |
| 14 | Gly | 108 |
| 15 | Ala | 124 |
| 16 | Gly | 140 |
| 17 | Asp | 116 |
| 18 | Tyr | 105 |
| 19 | Leu | 118 |
| 20 | Leu | 182 |

EXAMPLE 6

(DNA Synthesis-inducing Activity of Purified hst-1 Mutein N27)

The DNA synthesis-inducing activity of the purified hst-1 mutein N27 obtained in Example 1-c) above, on mouse BALB/c3T3 cells, was determined by the method described in Example 1-e). The results are shown in FIG. 10.

In FIG. 10, -□-,-○-and -Δ-show the results for bovine pituitary-derived FGF, hst-1 mutein N27 alone and hst-1 mutein N27 in combination with heparin (50 µg/ml), respectively. From FIG. 10, it is evident that hst-1 mutein N27 has an activity similar to that of bovine pituitary-derived FGF (produced by Takara Shuzo) and shows no heparin dependency.

EXAMPLE 7

(Cell Growth-promoting Activity of Purified hst-1 Mutein N27)

BALB/c3T3 cells were seeded on DMEM medium (produced by Flow Co.) supplemented with 5% FCS (produced by MBA) in a Linbro dish (produced by Flow Co.). Next day, the culture broth was replaced with DMEM medium supplemented with 0.5% FCS; at the same time a sample was added. Three days later, a cell count was taken. The results are shown in FIG. 11.

Figure 11:
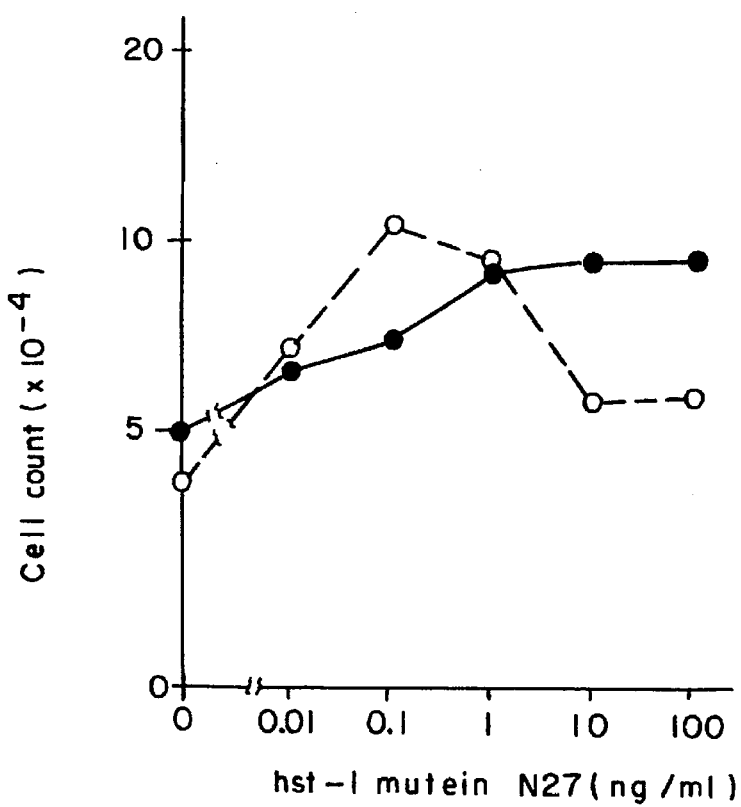
FIG. 11 shows the results of the cell growth-promoting activity, obtained in Example 7.

In FIG. 11, -●-and - - -○- - -show the results for hst-1 mutein N27 alone and hst-1 mutein N27 in combination with heparin (50 µg/ml), respectively. From FIG. 11, it is evident that hst-1 mutein N27 possesses cell growth-promoting activity and is potentiated by the addition of heparin.

EXAMPLE 8

(Stability under Acidic Conditions)

The hst-1 mutein N27 obtained in Example 1-c) (1 µg/ml) and rhbFGF were each kept at 37° C. and pH 4.0; residual activity was determined regularly by the method of Example 1-e). The results are shown in FIG. 12.

In FIG. 12, -○-and- . -□- . - show the results for hst-1 mutein N27 and bFGF, respectively; values are expressed in % ratio, the activity obtained at the commencement of incubation taken as 100%. These results show that hst-1 mutein N27 retains greater stability than bFGF under acidic conditions.

EXAMPLE 9

(Transforming Activity of hst-1 Mutein N27)

When mouse BALB/c3T3 A31 cells were cultivated in the presence of 10 ng/ml hst-1 mutein N27, a noticeable morphological change occurred like that found in transform cells. When heparin (25 μg/ml) was also added, a similar morphological change occurred at an hst-1 mutein N27 concentration of 1 ng/ml.

It was also found that hst-1 mutein N27 possesses colony forming activity, as follows: 0.3% agar medium containing $10^3$ BALB/c3T3 A31 cells in suspension was layered on 0.5 ml of 10% FCS-DMEM medium containing 0.5% agar (Bactoagar, Difco Co.) in a Linbro dish. About 2 weeks after incubation in a $CO_2$ incubator following addition of hst-1 mutein N27 at 100 to 1000 ng/ml to the agar medium, colony formation was observed at a frequency of 0.5 to $1 \times 10^{-2}$.

EXAMPLE 10
(Action on bFGF-receptor Binding)

The amino acid sequence of hst-1 mutein N27 of the present invention is homologous to that of bFGF. It was determined whether hst-1 mutein N27 inhibits the binding of bFGF to its receptor. A bFGF-receptor binding experiment was conducted in accordance with the method used in a binding test of another cell growth factor (TGF-B) by Wakefield [Methods in Enzymology, 146, 167 (1987)]. Rat C6 glioma cells (purchased from Dainippon Pharmaceutical) were used as target cells. The radiolabeled bFGF used was iodine-labeled bovine bFGF produced by Amersham Co. As a control, recombinant human bFGF (rhbFGF) obtained by the method described in European Patent Publication No. 237,966 was used. C6 glioma cells were cultivated on a 24-well culture plate. After culture medium was removed, a binding experiment buffer (Eagle MEM medium, 25 mM HEPES, pH 7.5, 0.15% gelatin, 5.0 μg/ml dextran sulfate) was added. 1.7 kBq of the iodine-labeled bFGF and a varying concentration of hst-1 mutein N27 or the control rhbFGF were added to achieve a reaction mixture amount of 300 μl, followed by reaction at 4° C. for 3 hours. After completion of the reaction, the reaction mixture was removed, and the plate was washed with Hank's balanced salt solution. After solubilizing the cell membrane with a 0.5% Triton-X100 solution, the radioactivity therein was determined using a gamma ray counter produced by Aloka. Separately, radioactivity was determined in the presence of 4.0 μg/ml rhbFGF in much excess in the reaction mixture; this value, as nonspecific binding amount, was subtracted from the radioactivity value obtained above to calculate the specific binding amount. This amount was divided by the specific radioactivity of the radiolabeled substance to calculate the rhbFGF concentration. Separately, the cells involved in the reaction were counted using a cell counter (Coulter counter ZM model, Coulter CO.). From these two figures, the amount of rhbFGF bound per cell was calculated. The results are shown in FIG. 13. In FIG. 13, the abscissa indicates the concentration of hst-1 mutein N27 added to the reaction mixture and the concentration of rhbFGF added as control in the binding experiment. The ordinate indicates the rhbFGF binding amount per $10^6$ cells involved in the reaction (femtomol= fmol) as calculated from the found value of radiolabeled rhbFGF amount after reaction completion, which corresponds to the amount of rhbFGF bound to the rhbFGF receptor. Solid line ● shows the results for hst-1 mutein N27 and dotted line ■ shows the results for rhbFGF.

As is evident from FIG. 13, the hst-1 mutein N27 of the present invention showed no inhibitory action on the binding of rhbFGF to its receptor.

The following references, which are referred to for their disclosures at various points in this application, are incorporated herein by reference:

Proc. Natl. Acad. Sci. USA, 85, 4861–5864 (1988)
Proc. Natl. Acad. Sci. USA, 83, 3997 (1986)
Proc. Natl. Acad. Sci. USA, 84, 7305 (1987) Oncogene, 3, 383 (1988)
Jpn. J. Cancer Res. (Gann) 78, 325 (1987)
Jpn. J. Cancer Res. (Gann) 78, 651 (1987)
Jpn. J. Cancer Res. (Gann) 78, 1036 (1987) Cell, 50, 729 (1987)
Proc. Natl. Acad. Sci. USA, 84, 2980–2984 (1987)
Molecular and Cellular Biology, 8, 2933–2941 (1988)
Bichemistry, 18, 5294 (1979)
Huynh, T. V. et al.: DNA Cloning, A Practical Approach, IRL Press, Oxford, p. 49 (1985)
Watson, C. J. and Jackson, J. F.: DNA Cloning, A Practical Approach, IRL Press, Oxford, p. 79 (1985)
Molecular Cloning, Cold Spring Harbor Laboratory, p. 320 (1982)
Proc. Natl. Acad. Sci. USA, 74, 560 (1977)
Nucleic Acids Research, 9, 309 (1981)
Advanced Bacterial Genetics, Cold Spring Harbor Laboratory, (1980)
Genetic Engineering, Academic Press, pp. 31–50 (1983)
Genetic Engineering, Principle and Methodology, Plenum Press, vol. 3, pp. 1–32 (1981)
Gene, 33, 103–119 (1985)
Methods in Enzymology, 101, 20–78 (1983)
Molecular and General Genetics, 177, 231 (1980)
Genetic Engineering, Plenum Press, vol. 3, pp. 1–32 (1981)
Gene, 2, 95, (1977)
Gene, 4, 121 (1978)
Gene, 19, 259 (1982)
Biochemical and Biophysical Research Communication, 122, 678 (1983)
Molecular Cloning, Cold Spring Harbor Laboratory, p. 239 (1982).
Proc. Natl. Acad. Sci. USA, 60, 160 (1968)
Nucleic Acids Research 9, 309 (1981)
Journal of Molecular Biology, 120, 517 (1978)
Journal of Molecular Biology, 41, 459 (1969)
Genetics, 39, 440 (1954)
Gene, 24, 255 (1983)
Journal of Biochemistry, 95, 87 (1984)
Cell, 23, 157 (1981)
Proc. Natl. Acad. Sci. USA, 69, 2110 (1972)
Gene, 17, 107 (1982)
Molecular and General Genetics, 168, 111 (1979)
Proc. Natl' Acad. Sci. USA, 75, 1929 (1978)
Virology, 52, 456 (1973)
Journal of Experiments in Molecular Genetics, 431–433, Cold Spring Harbor Laboratory, New York (1972)
Proc. Natl' Acad. Sci. USA, 77, 4505 (1980)
Science, 122, 501 (1952)
Virology, 8, 396 (1959)
Journal of the American Medical Association, 199, 519 (1967)
Proceedings of the Society for the Biological Medicine, 73, 1 (1950)
Gene, 56, 125–135 (1987)
J. Mol. Biol., 189, 113–130 (1986)
Mol. Cell Biol., 8, 588–594 (1988)
Methods in Enzymology, 146, 167 (1987)
European Patent Publication No. 237,966

What we claim is:

1. A deletion type mutein of heparin-binding secretory transforming factor (hst-1), wherein said mutein possesses hst-1 activities and lacks from 1 up to 47 continuous constituent amino acid residues selected from constituent amino acids 1 to 47 from the amino terminal constituent of hst-1 as shown in FIG. 1.

2. A mutein as claimed in claim 1, wherein said mutein lacks from 1 up to 46 continuous constituent amino acid residues selected from constituent amino acids 1 to 46 from the amino terminal of hst-1 as shown in FIG. 1.

3. A mutein as claimed in claim 1, wherein said mutein lacks from 1 up to 43 continuous constituent amino acid residues selected from constituent amino acids 1 to 43 from the amino terminal of hst-1 as shown in FIG. 1.

4. A mutein as claimed in claim 1, wherein said mutein lacks from 1 up to 27 continuous constituent amino acid residues selected from constituent amino acids 1 to 27 from the amino terminal of hst-1 as shown in FIG. 1.

* * * * *